(12) United States Patent
Thorne et al.

(10) Patent No.: US 7,542,546 B2
(45) Date of Patent: *Jun. 2, 2009

(54) SAMPLE MOUNTS FOR MICROCRYSTAL CRYSTALLOGRAPHY

(75) Inventors: Robert E. Thorne, Ithaca, NY (US); Zachary Stum, Niskayuna, NY (US); Kevin O'Neill, Rotterdam (NL); Jan Kmetko, Sunbury, OH (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/892,812

(22) Filed: Aug. 27, 2007

(65) Prior Publication Data

US 2008/0165929 A1  Jul. 10, 2008

Related U.S. Application Data

(63) Continuation of application No. 11/228,455, filed on Sep. 19, 2005, now Pat. No. 7,263,162, which is a continuation of application No. PCT/US2004/006088, filed on Mar. 22, 2004.

(60) Provisional application No. 60/455,853, filed on Mar. 20, 2003.

(51) Int. Cl.
  *G01N 23/20* (2006.01)
  *G21K 5/00* (2006.01)
  *A61B 6/08* (2006.01)
  *B23Q 1/00* (2006.01)
  *G01F 23/00* (2006.01)

(52) U.S. Cl. .............................. 378/79; 378/71; 378/73; 378/74; 378/80; 378/81; 378/205; 378/206; 378/208; 378/68; 269/47; 269/287; 269/900; 269/908; 269/909; 250/440.11; 250/442.11; 250/491.1; 29/281.1

(58) Field of Classification Search ................... 378/71, 378/73–74, 79–81, 68–69, 205–206, 208; 269/908–909, 900, 47, 287; 29/281.1; 250/440.11, 250/442.11, 491.1
See application file for complete search history.

(56) References Cited

U.S. PATENT DOCUMENTS 2,099,613 A * 11/1937 Loewus ........................ 15/427
2,345,723 A *  4/1944 Atlee et al. ................. 378/125
2,926,258 A *  2/1960 Weissmann .................. 378/74
3,105,901 A * 10/1963 Ladell et al. .................. 378/81

(Continued)

*Primary Examiner*—Robert M Kunemund
*Assistant Examiner*—G. Nagesh Rao
(74) *Attorney, Agent, or Firm*—Jones, Tullar & Cooper, P.C.

(57) ABSTRACT

Sample mounts (10) for mounting microcrystals of biological macromolecules for X-ray crystallography are prepared by using patterned thin polyimide films (12) that have curvature imparted thereto, for example, by being attached to a curved outer surface of a small metal rod (16). The patterned film (12) preferably includes a tip end (24) for holding a crystal. Preferably, a small sample aperture is disposed in the film for reception of the crystal. A second, larger aperture can also be provided that is connected to the sample aperture by a drainage channel, allowing removal of excess liquid and easier manipulation in viscous solutions. The curvature imparted to the film (12) increases the film's rigidity and allows a convenient scoop-like action for retrieving crystals. The polyimide contributes minimally to background and absorption, and can be treated to obtain desired hydrophobicity or hydrophilicity.

20 Claims, 3 Drawing Sheets

U.S. PATENT DOCUMENTS

| | | | |
|---|---|---|---|
| 3,160,748 A * | 12/1964 | Chan | 378/81 |
| 3,230,365 A * | 1/1966 | Nagahama | 250/442.11 |
| 3,240,934 A * | 3/1966 | Watanabe et al. | 250/442.11 |
| 3,340,396 A * | 9/1967 | Prickett et al. | 378/75 |
| 3,564,240 A * | 2/1971 | Thomas, Jr. | 378/81 |
| 4,264,385 A * | 4/1981 | Fisher | 117/17 |
| 4,759,130 A * | 7/1988 | Goldowsky | 33/1 N |
| 6,185,276 B1 * | 2/2001 | Eastman | 378/143 |
| 6,404,849 B1 * | 6/2002 | Olson et al. | 378/79 |
| 6,506,277 B2 * | 1/2003 | Roeker et al. | 156/299 |
| 6,608,883 B2 * | 8/2003 | Olson et al. | 378/79 |
| 6,677,162 B1 * | 1/2004 | Wendelbo et al. | 436/174 |
| 6,918,698 B2 * | 7/2005 | Nordmeyer et al. | 378/205 |
| 6,968,037 B2 * | 11/2005 | Rosso et al. | 378/79 |
| 7,038,218 B2 * | 5/2006 | Lee et al. | 250/440.11 |
| 7,263,162 B2 * | 8/2007 | Thorne et al. | 378/79 |
| 7,311,773 B2 * | 12/2007 | Sanjoh | 117/68 |
| 2002/0171044 A1 * | 11/2002 | Carroll | 250/442.11 |
| 2003/0152194 A1 * | 8/2003 | Nordmeyer et al. | 378/73 |
| 2004/0008814 A1 * | 1/2004 | Shafer | 378/79 |
| 2004/0234030 A1 * | 11/2004 | Miller et al. | 378/79 |
| 2004/0258203 A1 * | 12/2004 | Yamano et al. | 378/73 |
| 2005/0035303 A1 * | 2/2005 | Ham | 250/442.11 |
| 2005/0087697 A1 * | 4/2005 | Lee et al. | 250/440.11 |
| 2005/0163280 A1 * | 7/2005 | Nordmeyer et al. | 378/71 |
| 2006/0086315 A1 * | 4/2006 | Thorne et al. | 117/209 |

* cited by examiner

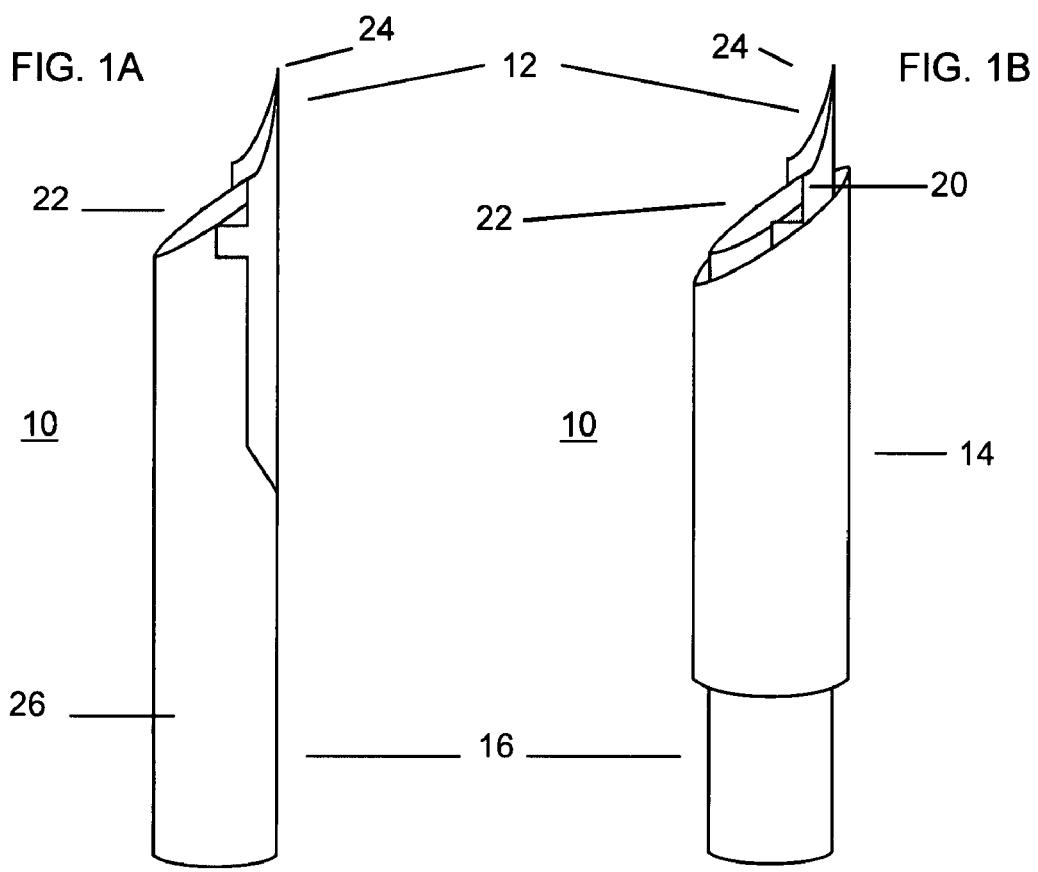
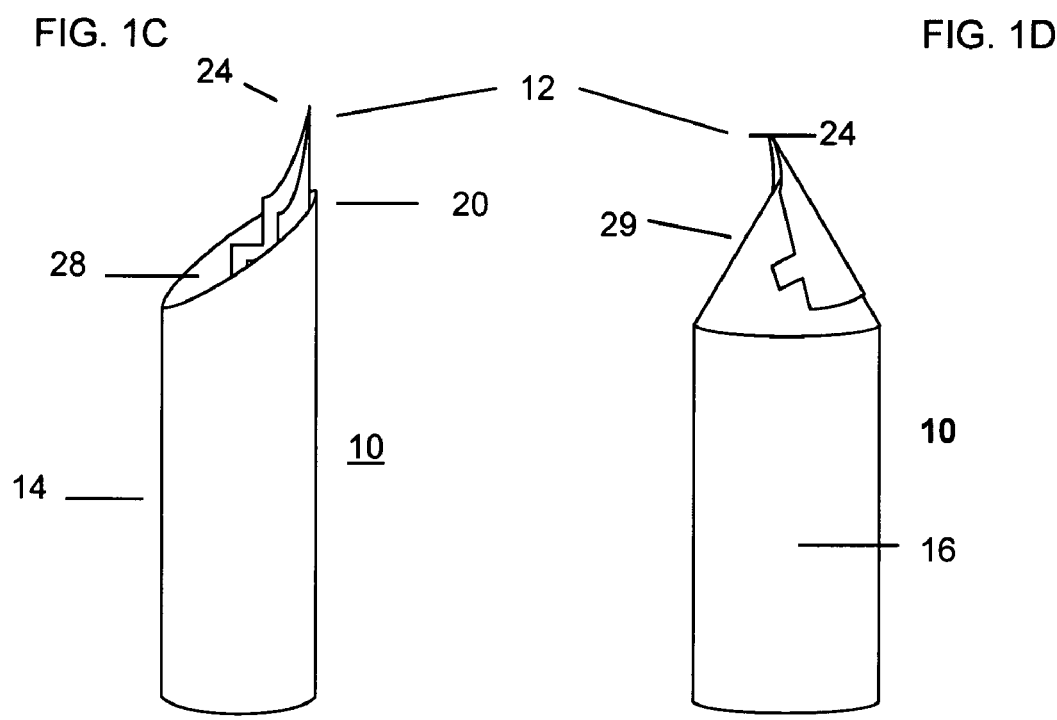

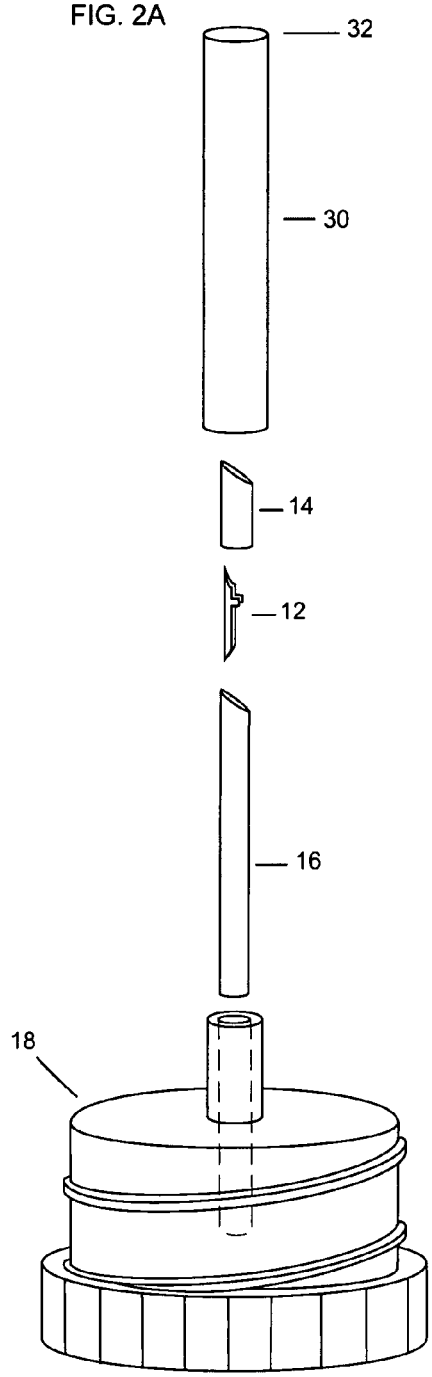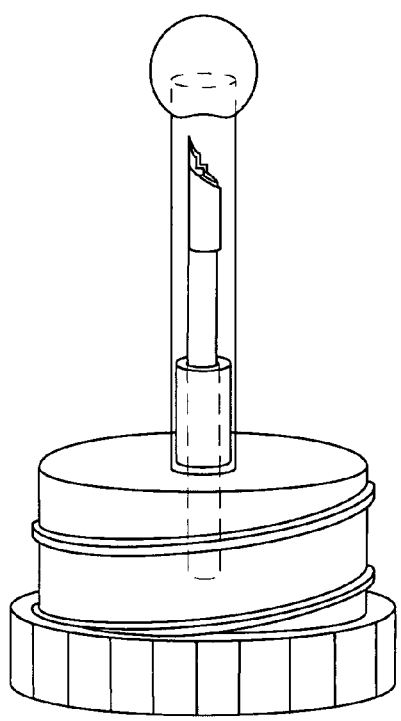

SAMPLE MOUNTS FOR MICROCRYSTAL CRYSTALLOGRAPHY

CROSS REFERENCE TO RELATED APPLICATIONS

This application is a continuation under 35 U.S.C. 120 of U.S. application Ser. No. 11/228,455, filed Sep. 19, 2005, to issue as U.S. Pat. No. 7,263,162 on Aug. 28, 2007, which is a continuation under 35 U.S.C. 120 and 365(c) of International Application No. PCT/US2004/006088, filed Mar. 22, 2004, which claims the benefit under 35 U.S.C. 119(e) of U.S. Application No. 60/455,853, filed Mar. 20, 2003.

GOVERNMENT SPONSORSHIP STATEMENT

This invention was made with Government support from the National Institutes of Health (NIH) under grant number GM065981 and the National Aeronautics and Space Administration (NASA) under grant number NAG8-1831. The Government has certain rights in the invention.

BACKGROUND OF THE INVENTION

1. Field of the Invention

The present invention relates in general to sample mounts for mounting and manipulating macromolecular and virus crystals and other samples for X-ray crystallography, and methods of using the same.

2. Description of the Background Art

One of the most common ways of mounting crystals for X-ray data collection and structure determination is to insert them into thin-walled (typically 10 micrometer) glass or quartz capillaries. These thin capillaries are X-ray transparent and produce relatively little background scatter. They can be sealed at both ends, providing a stable environment for the crystal. This is particularly important for crystals of proteins and other biological macromolecules, which contain large amounts of solvent (mostly water) and must be maintained in a constant humidity environment to preserve their structure and order. The environment of the crystal can be changed inside the capillary. For example, crystals can be controllably dehydrated by injecting a small amount of a saturated salt solution into the capillary. Crystals can also be soaked inside the capillary in solutions containing drug molecules, small molecule ligands, and heavy atom compounds. Capillary mounted crystals can be used for data collection from the melting point of the crystal solvent to well above room temperature. They are particularly important for crystals that cannot be flash frozen for data collection without inducing excessive crystal disorder.

In a known technique used to mount protein and other biomolecular crystals in capillaries, a capillary of diameter comparable to the crystal diameter is first selected, in order that the final mounted crystal lie near the center of the capillary to simplify alignment in the X-ray beam. Next, the sealed end of the capillary is scored and broken, and some means for producing suction attached to the other, larger diameter end. The open end of the capillary is inserted into the liquid drop in which the crystal resides and a small amount of this liquid is pulled into the capillary. The capillary is removed from the liquid and a small amount of air is pulled in to move the liquid away from the end. Next, the capillary is inserted back into the liquid drop and the crystal is carefully sucked in. Excess liquid surrounding the crystal is removed using paper wicks, and the open end of the capillary sealed with wax, grease, etc. The suction device is removed from the large diameter end, the capillary is scribed and broken to the desired length, the end is sealed and then the capillary is mounted onto a pin or goniometer head, typically using modeling clay, for X-ray measurements.

Another area where crystal mounting and manipulation is employed is in X-ray cryocrystallography, which is extensively used for crystals of proteins, protein-nucleic acid complexes and viruses and other crystals that are sensitive to radiation damage by X-rays. The development and application of cryocrystallographic techniques has had a dramatic impact on the rate at which structures of biological macromolecules and macromolecular complexes can be solved. Much larger X-ray doses can be absorbed before radiation damage becomes significant, so that complete data sets can often be collected using a single crystal.

A variety of methods have been used to manipulate mount crystals for flash cooling and cryocrystallographic data collection. Early experiments attached crystals to the ends of glass fibers or placed them on top of miniature glass spatulas. A loop mounting method using low X-ray absorption materials for the loop is now by far the most widely used method for manipulating and mounting crystals. Loop cryomounts consist of a small (10-20 $\mu$m) diameter nylon (or metal) line that is twisted to form a loop and then threaded into a small hollow metal rod. This rod is then inserted into a metal or plastic goniometer-compatible base. Crystals are retrieved from the mother liquor in which they are grown by capturing them in the loop, and then they are transferred using the loop between one or more solutions including stabilizing solutions, heavy atom compound solutions, solutions containing small molecules, drugs or ligands, or cryoprotectant solutions. Crystals larger than the loop can rest on its surface, while smaller crystals can be trapped in the liquid film that spans the loop or else adhered to the side of the loop. Loop-mounted crystals are then flash cooled by immersion in liquid nitrogen or propane or by insertion in a cold gas stream.

Loops provide convenient crystal manipulation. By holding crystals in the liquid film of the loop, potentially damaging contact with hard surfaces (such as those of alternative mounting tools) is minimized. The loop itself is flexible enough to make damage due to incidental contact less severe. Loops help minimize thermal mass and maximize surface area for heat transfer, increasing cooling rates and thus reducing cryoprotectant concentrations needed to prevent hexagonal ice formation within and surrounding the crystal. For these reasons loop-based mounts have been chosen as the standard for high-throughput automated cryocrystallography at synchrotron X-ray beam lines around the world.

The foregoing known techniques for mounting samples in crystallography applications have a number of drawbacks. In particular, the capillary mounting technique requires that both the initially sealed and wide diameter open end of the capillary must be cut and then subsequently sealed. These manipulations increase the chance that the capillary will be broken and the crystal inside damaged. In addition, the minimum capillary wall thickness that can be used and still provide adequate robustness for cutting is limited to about 10 micrometers. This in turn fixes the capillary's contribution to background X-ray scatter, which can significantly degrade the overall signal-to-noise ratio when measuring very small crystals.

For very small crystals (<50 micrometers), wicking away excess liquid without disturbing the crystal is difficult. Residual liquid between the crystal and capillary wall may have a volume comparable to the crystal volume (because of the larger surface to volume ratio of small crystals), which will increase background scattering of X-rays. Any residual liquid between the crystal and capillary also acts with the curved capillary wall as a distorting lens that makes accurate crystal alignment in the X-ray beam difficult. While some liquid is required to hold the crystal in place against the capillary wall, if there is excess liquid, the crystal may slip relative to the wall during diffraction measurements, which can create errors in data analysis.

To ensure that the crystal ends up near the radial center of the capillary, the capillary diameter must be matched to the crystal size. Consequently, capillaries of many diameters must be stocked. Even with a correctly sized capillary, the vertical and horizontal position of the crystal relative to the axis of the X-ray system is poorly controlled, requiring time-consuming alignment for each crystal. Positioning the crystal at a particular distance, e.g., from the base to be mounted in the goniometer head requires careful crystal manipulation and careful cutting of capillaries, which can be very time consuming. Adjustment of pressure in the suction device during crystal retrieval also requires considerable skill. Because of their large size, capillaries can obstruct the view of the crystal to be mounted, and are difficult to manipulate in small drops. Contact with the capillary ends and walls during retrieval often damages crystals (especially those with plate-like geometries), increasing their mosaicity and degrading their X-ray diffraction properties. Although possible, retrieving crystals from capillaries for further treatment or measurement is extremely difficult. Soaking crystals in ligands, drugs or heavy-atom compounds after data collection of a native structure can be performed in the capillary, but is inconvenient and often displaces the crystal.

In cryocrystallography, the use of loop mounts is also problematic. In particular, loops are quite flexible, especially those made using 10 μm diameter nylon line. As a result, loops can bend under liquid and surface tension forces during crystal retrieval from solution, and they can bend under the weight of the crystal and surrounding liquid once a crystal is mounted. Because of their irregular aerodynamic profile they can bend and flutter under the drag forces of the cryostream, slightly broadening X-ray diffraction peaks for the lowest mosaicity crystals and reducing the maximum diffraction signal-to-noise achieved when crystal mosaicity and incident beam divergence are matched.

In addition, loops provide poor crystal positioning accuracy and reproducibility relative to the X-ray spindle axis. The loop shape for a given nominal loop diameter is irregular and irreproducible. The loop orientation relative to the metal post through which they are threaded is irregular, in part due to the twist of the nylon at their base needed to improve rigidity. Crystal positioning within the loop is irreproducible, especially for very small crystals. The crystal and the loop itself (which gains rigidity from frozen liquid) can shift during in situ crystal "annealing" or "tempering" protocols that raise the sample temperature near or above the melting point/glass transition of the surrounding solvent, necessitating crystal realignment in the X-ray beam.

Loops can also trap significant liquid around the crystal. This liquid can be difficult to wick away, especially if the crystal is smaller than the loop's inner area. Remaining liquid increases background scattering, reducing diffraction signal-to-noise, and increases thermal mass, thereby decreasing cooling rates. Moreover, surrounding liquid has different freezing properties and thermal expansion behavior than the crystal and can exert damaging forces during cooling. Frozen surrounding liquid also can make small (less than 50 μm) crystals difficult to image and align.

The limitations of loops are becoming increasingly apparent as crystallographers attempt structural studies using smaller and smaller crystals made possible by continuing improvements in X-ray sources, optics and detectors. Initial crystallization trials—especially those based on high-throughput robotic screening—usually yield very small crystals. Collecting X-ray data from these crystals can provide valuable feedback early in the growth optimization process, and sometimes immediately yields useful structural information. Crystal size may remain small even after substantial optimization of crystal quality, especially in the case of macromolecular complexes and membrane proteins. Despite reduced signal-to-noise and increased radiation damage, smaller crystals may even be desirable because they flash cool more rapidly and thus are easier to cryoprotect; they can yield better diffraction data sets than larger crystals unless cryoprotection conditions for the latter are carefully optimized.

For crystals with sizes below 50 μm, loops become extremely difficult to use. Flexibility constraints limit the minimum nylon diameter, which in turn limits the minimum inner loop diameter. Smaller crystals must often be held in a liquid meniscus of larger volume, reducing diffraction signal-to-noise and making alignment more difficult. Large liquid-to-crystal volume ratios also limit reductions in thermal mass and cooling times.

In view of the foregoing, a need remains for improved techniques for mounting microcrystals for use in X-ray crystallography and cryocrystallography applications.

SUMMARY OF THE INVENTION

The present invention addresses the foregoing need through provision of microcrystal sample mounts in which a thin plastic film is employed to support a crystal to be analyzed. The film has a thickness of 50 μm or less and is preferably made from polyimide. A key feature of the invention is that a curvature is imparted to the film to increase its structural rigidity substantially. The increase in rigidity enables the use of thinner films with thicknesses on the order of 3-15 μm (or even thinner, provided other mount dimensions are correspondingly reduced), which reduces background scattering of the X-rays.

To provide the requisite curvature, a number of techniques can be employed, depending upon the type of crystallography application. In cryocrystallography applications, where capillary tubes are not employed, the polyimide film is preferably mounted either to an external curved surface of a rod or pin, the internal curved surface of a hollow rod or sleeve, or between both a sleeve and a rod. In these embodiments, the rod and/or hollow sleeve preferably have beveled top ends to maximize the viewing angle of the sample position so that one can see crystals and any crystal aperture when the rod, sleeve and mount are angled relative to the horizontal. Alternatively, the film can be attached to a rod having a conical end such that the plastic mount is tilted relative to the rod, so that it is easier to scrape a crystal off a flat surface and the crystal is located on axis, which makes alignment even easier.

In crystallography applications that use capillary tubes, the curvature can also be imparted by making the film large enough that the capillary itself will impart the requisite curvature when the film is inserted therein. In this variation, a suitable tool, such as a pair of forceps, can be employed to impart the curvature initially to the film so that it can be inserted into the capillary or tube.

Polyimide is a good choice for the film material because of its excellent mechanical properties; because it has a low density and is composed of low atomic number elements so that it scatters X-rays very weakly; and because its gold hue provides good optical contrast with macromolecular crystals.

The polyimide films are microfabricated to have a tapered tip end for holding a crystal to be examined. This tapering minimizes the volume of the film in the X-ray beam (whose size is usually matched to or smaller than the crystal size) when the plane of the film is oriented parallel to the beam. Preferably, a first sample aperture is disposed at the tip end for reception of the crystal, though the aperture is not essential. This aperture allows the crystal to be precisely located, and further minimizes the volume of the film in the X-ray beam and thus the background scatter from the film. For mounts intended for cryocrystallography of macromolecular or virus crystals grown in solution, a small channel is preferably disposed in the film that connects the sample aperture to a larger aperture which facilitates wicking of any excess fluid from the sample aperture with little risk of touching the crystal. The large aperture also reduces the total area of polyimide and thus reduces the fluid resistance and flow disturbances caused as the mount is moved through a crystal-containing drop. The channel and large aperture are not necessary for "dry" crystals of inorganic or small-molecule organic materials where excess fluid is not an issue.

The film preferably has a small fixed width (5-100 μm, depending on the size of the crystals to be examined) surrounding the sample aperture that reduces scattering from the polyimide film (and any adsorbed fluid) when the plane of the film is oriented parallel to the X-ray beam. An overall triangular shape of a top portion of the film that is intended to extend beyond the rod or sleeve to which it is attached, together with a tapered or beveled shape of the rod or sleeve, provides a good aerodynamic profile that minimizes sample "flutter" in a gas cooling stream (relevant for lowest mosaicity crystals).

The present invention thus provides an alternative to conventional loops that retains all of their advantages (including complete compatibility with existing and developing technologies for high-throughput crystallography), but that resolves most if not all of the problems in mounting smaller crystals. Their potential advantages include completely reproducible sample "loop" sizes down to 3 micrometers or even smaller if thinner, shorter films with larger curvature are used, accurate and reproducible sample positioning, good sample-mount contrast, easier removal of excess liquid, minimal thermal mass and more rapid flash cooling; reduced background scattering, and easy design customization and mass production. In addition, the color, rigidity and reproducibility of the mounts should make it feasible to retrieve crystals using robots, with large savings in labor. In contrast, the use of loop type mounts requires that all crystals be retrieved by hand from crystallization drops, because loops are floppy and have little contrast with drop solutions.

BRIEF DESCRIPTION OF THE DRAWINGS

The features and advantages of the present invention will become apparent from the following detailed description of a number of preferred embodiments thereof, taken in conjunction with the accompanying drawings, in which:

FIGS. 1A-1D are illustrations of four microcrystal sample mounts that are constructed in accordance with the preferred embodiments of the present invention;

FIGS. 2A and 2B are exploded and assembled views, respectively, of an assembly using one of the preferred sample mounts to position a microcrystal in a controlled environment capillary or tube using a base compatible with standard X-ray equipment.

DETAILED DESCRIPTION OF THE PREFERRED EMBODIMENTS

Figure 3:
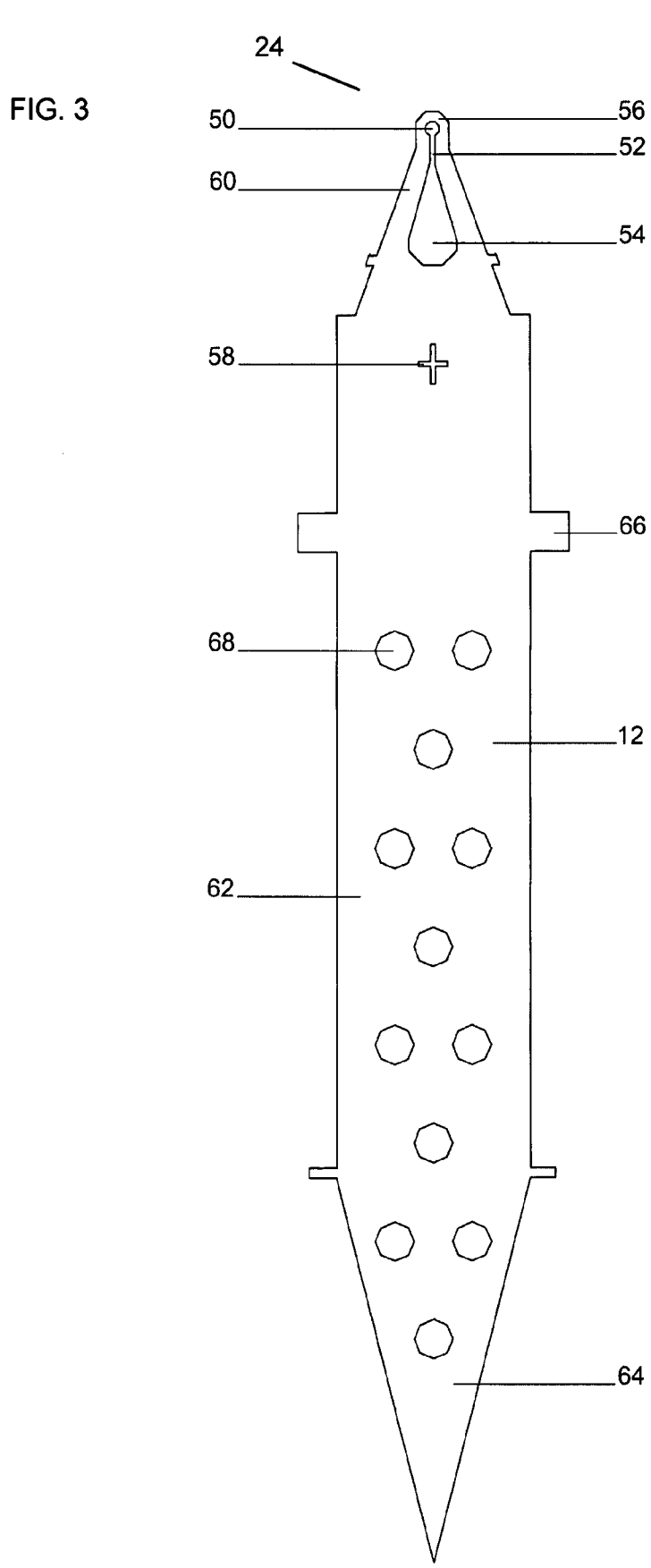
FIG. 3 is an illustration of a patterned polyimide film that forms the actual crystal mount in the preferred embodiments of the invention.

With reference to FIGS. 1A-1D, several variations of a microcrystal mount 10 are illustrated that are constructed in accordance with four preferred embodiments of the invention and are each designed particularly for use with a goniometer or other standard sample holder/positioner used in X-ray crystallography. In each embodiment, the mount 10 includes a microfabricated plastic film 12 that is attached to a structure having a curved surface such that curvature is imparted to the film 12. In the embodiment of FIG. 1A, the film 12 is attached by any suitable means, such as adhesive, tape, thermal bonding or the like, to a small diameter cylindrical plastic or metal post 16. As illustrated in FIG. 2A, the post 16 is sized to be inserted into standard plastic or metal magnetic goniometer head mount 18, such as those sold by Hampton Research or being developed by the macromolecular crystallography community for high-throughput automated crystallography, or into keyed variants of these allowing for higher precision alignment of the film 12 and the post 16 relative to the goniometer head (not shown). The film 12 has a tapered end that tapers to a tip 24 and forms a scoop shape when attached to the rod 16.

In the embodiment illustrated in FIG. 1B, a hollow metal or plastic sleeve or rod 14 is also employed in conjunction with the rod 16 such that the film 12 is held between these two elements. The sleeve 14 rigidly attaches the film 12 to an outside curved surface 26 of the rod 16 and forces the film 12 to conform to the rod's curvature while allowing easy assembly. Preferably, a small amount of glue is used to seal the area between the sleeve 14 and the rod 16 and fix the sleeve 14 relative to the rod 16. Alternatively, the sleeve 14 can be implemented using heat-shrinkable tubing that will grip the film 12 between the sleeve 14 and the rod 16. Still further, as illustrated in FIG. 1C, the hollow sleeve 14 can be used by itself such that the film 12 is attached, e.g. by adhesive, tape, thermal bonding, etc. to the inside curved surface 28 of the hollow sleeve 14. The film 12 can also be crimped to the inside curved surface of the sleeve 14 by collapsing one side of the sleeve so that it squeezes the film against the other curved side.

In both of the embodiments illustrated in FIGS. 1A and 1B, the sleeve 14 and the rod 16 preferably have beveled top ends 20 and 22, respectively, to maximize the viewing angle of the sample position, which is located at the tip end 24 of the polyimide film 12 as discussed in greater detail later in conjunction with FIG. 3. An alternative embodiment which achieves the same goal is illustrated in FIG. 1D in which the rod 16 has a conical top end 29 to which the film 12 is attached. As shown, the film 12 is mounted at an angle relative to the vertical longitudinal axis of the rod 16 such that the tip end 24 of the film is positioned directly over this axis. As a result, alignment of the film 12 is made easier. More importantly, the angling of the film 12 positions its scoop shaped tip in such a way that scraping of crystal off of a flat surface is made easier.

The curvature of the polyimide film 12 that is imparted by any of the preferred embodiments dramatically increases its bending rigidity; a cylindrically curved piece of paper is much harder to bend than a flat one. This extra rigidity is crucial in allowing the film 12 to be made very thin, on the order of 3-15 μm, thereby minimizing background scatter from the polyimide film 12 and allowing film patterning to the small lateral dimensions required for mounting the smallest crystals. As just noted, this curvature also produces a convenient, gentle scoop-like action when retrieving crystals and for transferring crystals between solutions that minimizes the chance of crystal damage.

For room temperature crystallography applications where the sample crystal is to be maintained in a controlled environment, a plastic tube or glass X-ray capillary 30 is slid over the mount 10 and a tip end 32 of the tube 30 is then sealed as illustrated in FIG. 2B. In this embodiment, both the hollow sleeve 14 and the rod 16 need not be used if desired. Instead, the polyimide film 12 can be held by a pair of forceps that impose the desired curvature on the film 12. The film 12 is then inserted into an X-ray capillary 30 using the forceps. When the forceps are released, the curvature of the film 12 relaxes. The film width is chosen to be slightly larger than the capillary inside diameter so that the film 12 is held in place near the center of the capillary by its spring-like action. The end 32 of the capillary 30 can then be sealed using grease or wax. Additional liquid can be inserted into the capillary before sealing as desired.

In the event that the sleeve 14 and or rod 16 are employed to support the film 12, the X-ray capillary 30 with the narrow end cut is carefully pulled over the crystal and down onto the base 18. The base 18 may be lubricated with oil or grease and a rubber or silicone washer/O-ring pulled over the end of the capillary to provide an airtight seal with the capillary. The cylindrical portion over which the capillary is pulled can be an integral part of the base that attaches to the X-ray apparatus, or can be a separate cylindrical piece with a hole through which the rod is inserted into the base, with any gap between rod and the inside diameter of the hole sealed with grease. The narrow end is then sealed using grease, wax, glue, etc. Alternatively, the glass capillary 30 can be replaced with thin walled plastic tubing. For example, Advanced Polymers Incorporated of Salem, NH manufactures regular and low-temperature heat-shrinkable semi rigid transparent tubing with wall thicknesses of 0.0002 inches or 5 micrometers. In this case the tubing is pulled over the crystal and onto the base. Sealing both ends can be done with grease or oil, and/or in the case of low-temperature heat-shrinkable tubing using a variable temperature soldering iron with a custom curved tip. A small plug of any material can be inserted in the open end before sealing to improve the seal. In both cases, additional liquid can be inserted into the capillary/plastic tube before sealing. Also in both cases, the diameter of the capillary or plastic tube can be much larger than the width of the sample mount, making it easy to slide the capillary or plastic tube over the sample without disturbing it.

In all three of the above cases, but with particular ease in the second and third methods, which are preferred, crystals can be removed from the capillary/tube after X-ray data collection and subjected to other manipulations such as soaking in ligand, drug, or heavy atom solutions and then easily reinserted for additional data collection.

FIG. 3 shows a typical pattern for the polyimide film 12. It should be noted that the film 12 can also be made of any other suitable plastic or other material, but polyimide, which has low density, low atomic numbers of its constituents, and therefore low X-ray absorption and scattering, which is widely used (in the form of KAPTON tape) for temporary windows on X-ray beamlines, and which is readily patterned using microlithographic techniques of the microelectronics industry, is the preferred choice. In addition, the good contrast between the yellow-gold polyimide film and a crystal makes locating and aligning the crystal easier. The film 12 preferably includes a small sample aperture 50 at the narrow tip end 24 for holding a sample crystal to be analyzed or examined. The sample aperture 50 is preferably connected via a channel 52 to a much larger aperture 54. This structure allows a paper wick inserted into the large aperture 54 to remove excess fluid from around the crystal via the channel 52 with little risk of touching the crystal. The large aperture 54 also reduces the total area of polyimide and thus reduces the fluid resistance and flow disturbances caused as the mount is moved through a crystal-containing drop. Alternatively, neither of the apertures 50 and 54, nor the channel 52 need to be employed as a crystal to be examined can also be attached directly to the tip end 24 of the film 12, either by means of a droplet of liquid or a polymer, for example.

The film 12 has a rim 56 of small width surrounding the sample aperture 50 that reduces scattering from the polyimide film 12 (and any adsorbed fluid) when the plane of the film 12 is oriented parallel to the X-ray beam. Preferably, the rim 56 has a fixed width of between 5 and 100 μm that depends on the size of the crystal to be examined. A small cross-shaped aperture 58 is centered in the film 12 beneath the sample aperture 52 and the large aperture 54 that can be used to assist automated alignment. Other alignment apertures can be added to suit the alignment algorithm to be used. The overall triangular shape of a top portion 60 of the film which extends beyond the post 16, together with the post's tapered shape provides a good aerodynamic profile that minimizes sample "flutter" in a gas cooling stream (relevant for lowest mosaicity crystals.) The sample aperture 52 can be customized to any shape so as to simplify mounting of, e.g., rod-shaped crystals. The film thickness can also be varied, e.g., to produce ridges surrounding the sample aperture 52, to provide a stiffer base, or to modify the aerodynamics, but a uniform thickness provides more than adequate performance.

For ease of assembly, especially for attachment to the inside of the hollow sleeve 14, the film 12 includes an extended tail 62 with a tapered end 64 that allows easy insertion of the film 12 either into the sleeve 14, or in the case of a capillary application, into the plastic tube or capillary 30. A pair of small wings 66 stick out when the film 12 is inserted into the sleeve 14 and limit its travel into the sleeve 14, providing reproducible positioning. For films to be attached to the outside of the rod 16, a shorter, broader tail with a square end can be used. In both cases, the tail can be perforated with small apertures 68 to improve gluing strength. In addition, in a controlled atmosphere capillary embodiment, the apertures 68 trap small liquid drops when the film 12 is placed in a crystal-containing drop that later serve to maintain a humid environment in the capillary 30. For the thinnest polyimide films, all right angle cuts in the design—which are points of stress concentration—can be replaced with curves of finite radius to improve film robustness against tearing.

To fabricate the patterned polyimide films, a number of different processes can be employed, depending on the desired crystal aperture size and film thickness. A first, preferred film fabrication process is based on photodefinable polyimide and can produce much smaller aperture sizes. To begin, a ½μm silicon dioxide layer, to be used as a sacrificial layer during film lift-off, is deposited onto the surface of a clean silicon wafer. The wafer is spin-coated with positive tone photoexposable PWDC1000 polyimide. Standard processes such as pre-coating with an adhesion promoter or pre-baking in a vapor-priming oven ensure good adhesion between the wafer and polyimide. After a brief bake, the polyimide is soft-contact exposed through a chromium-glass mask containing the mount's pattern, and then submerged in developer to remove the exposed polyimide. The remaining patterned polyimide is then cured in a nitrogen-atmosphere oven. Finally, the wafer is submerged in dilute HF to remove the sacrificial silicon dioxide layer, allowing the patterned polyimide film to float free of the wafer. This process is suitable for fabricating polyimide films with thicknesses of 3-15 μm, which can then be patterned to an aperture size of 5 μm, which is suitable for mounting the smallest macromolecular crystals from which diffraction can currently be obtained. Thinner films and smaller aperture sizes can be obtained while maintaining adequate film rigidity by reducing the film's lateral dimensions and increasing its curvature. In a test setup using a 3 inch silicon wafer with a patterned polyimide film, 130 sample mounts can be produced at a time. With 8 inch wafers this number can be increased to over 1000, making the individual mounts very inexpensive to produce. Other common microfabrication processes such as contact printing and spray ("inkjet") printing could also be used, especially for mounts with larger aperture sizes.

For sample apertures larger than 50 μm, a fabrication process based on the copper-polyimide-copper sheet material used for flexible electronic circuits can be employed. A silicon wafer is spin-coated with photoresist and a piece of this sheet material matching the wafer size is pressed on top using a piece of glass to ensure a flat surface. This assembly is then baked to cure the photoresist and firmly attach the copper-polyimide-copper to the wafer. A second layer of photoresist is then applied on top of the copper and the wafer baked a second time. This layer is exposed in a broad-band UV contact aligner through a chromium glass mask containing the sample mount pattern (replicated to cover the wafer area) and then developed to remove the exposed photoresist. The pattern is etched into the top copper layer using ferric chloride, and is then etched into the polyimide using an $O_2$—$CHF_3$ gas plasma etch, after which the patterned copper-polyimide-copper film detaches from the wafer. The patterned sheet is placed in a bath of Shipley 1165 to remove residual photoresist and then into a second ferric chloride bath to etch away all remaining copper on the top and bottom of the polyimide film.

The minimum feature (e.g., aperture) size conveniently obtained by the subject process is limited by the non-vertical etch profiles and by the minimum copper (9 μm) and polyimide (25 μm) thicknesses of commercially available flexible circuit materials to about 50 μm.

Optionally, the surface properties of the fabricated polyimide films can be modified to improve the performance of the mounts in different solutions. Polyimide is naturally hydrophobic. In this state, the sample mounts tend to repel the mother liquor of soluble proteins and can cause disturbance of protein crystal-containing droplets. A broad variety of techniques have been developed to modify the surface properties of polyimide. To make the subject polyimide films hydrophilic, the preferred process is to expose them briefly to an oxygen gas plasma etch after lift off and drying. This treatment minimizes drop disturbances and allows crystals to be easily retrieved. However, with practice untreated mounts appear to perform nearly as well and reduce excess liquid, and their hydrophobic properties may be more useful for drops containing detergents.

Tests were conducted to compare the diffuse X-ray background versus resolution produced by a prior art 20 μm nylon loop mount and a 9 μm thick polyimide mount constructed in accordance with the preferred embodiments of the present invention. The tests established that the more rigid polyimide mount provides much less background scatter—especially in the important 2-5 Å resolution range. In general, the scoop-like action together with the reproducibility of the sample opening's size, shape and orientation make the subject mounts much easier to use than loops, especially for small crystals. As an example, the mounts have been used to mount and obtain a complete data set from a 5-7 μm macromolecular crystal. The subject mounts can also be used for large crystals with sizes of hundreds of micrometers, provided thicker polyimide films (10-25 μm) are used. Because of the small volume of polyimide in the beam path for all sample and mount orientations and polyimide's low density and atomic number composition, its contribution to background scatter is small compared with that from disordered internal and external solvent even for very small crystals. This volume can be reduced by optimizing the balance between film thickness (which determines bending rigidity) and the width of polyimide around the sample aperture. The same basic design fabricated by a thin film process should be applicable down to sample apertures of a few micrometers or less, provided the film thickness is reduced to account for the etch profile and the lateral mount dimensions are reduced to prevent buckling. For extremely small crystals the aperture can be eliminated, and a small curved solid area at the tip can be used to retrieve and support the crystal.

Another major advantage of the mounts constructed in accordance with the preferred embodiments is that they are much more rigid than loops. They remain rigid when submerged in crystal containing drops, simplifying crystal retrieval. They do not collapse during "annealing" or "tempering" procedures used to improve diffraction quality, and show no evidence of mosaicity broadening due to flutter in the cryostream. Finally, it should be noted that these microfabricated mounts should be more generally useful for small crystals of all kinds, both organic and inorganic. For "dry" crystals the wicking aperture can be eliminated as noted previously, and crystals can be firmly attached using glue or grease, or using a small drop of an ethyl cellulose—ethyl acetate mixture which can be washed away after data collection.

Numerous additional variations or modifications could be made to the preferred embodiments. For example, the films could be fabricated using other polymers, or two or more layers of different polymers to give better rigidity. The surface of the film can be patterned to produce a ribbed structure for better rigidity and bending characteristics with minimum total mass. In addition, the surface can be chemically treated, for example, to make the sample aperture water repellant and the "wicking" aperture water attractive. Pattern alignment marks can be disposed on the film around the sample aperture to facilitate automated alignment of the crystal. To facilitate different sized crystals, the sample aperture size can be made any size, and multiple sizes can be made on a single polyimide sheet. The width of polyimide around the aperture can then be minimized for each crystal size, minimizing the amount of X-ray scattering from the aperture. Where the support includes use of a cylindrical rod, the rod can be made hollow and of a low-specific heat, high thermal conductivity material to minimize thermal mass and evaporation of nitrogen during plunge cooling. Finally, the end of the rod where the film is attached can be tapered so that the film bends into part of a cone rather than part of a cylinder. By correct choice of aperture size for a given sample size and by choosing the angle of the rod's taper, the crystal can be placed on the axis of rotation of the sample mount/goniometer.

In conclusion, the present invention comprises a new approach to mounting crystals for macromolecular cryocrystallography that maintains the many advantages of the nylon loops now in wide use and at the same time resolves most of their deficiencies. Microfabricated polyimide film sample mounts are better suited to handling the very small crystals that can now be characterized at state-of-the-art synchrotron beam lines and that are being produced in abundance via automated crystallization at structural genomics centers. These mounts should simplify automation of X-ray data collection, and are better suited than existing alternatives for automated crystal retrieval from liquid droplets. Because their fabrication is based on standard microelectronics industry processes, these mounts should be easy and inexpensive to produce in quantities of millions per year that will soon be required by worldwide structural genomics efforts. They should be more generally useful for small organic/inorganic crystals of all sorts, and especially those of small organic/biological molecules that benefit from cryocooling for X-ray data collection.

Although the invention has been disclosed in terms of a number of preferred embodiment and numerous variations thereon, it will be understood that numerous additional modifications and variations could be made thereto without departing from the scope of the invention as defined in the following claims.

The invention claimed is:

1. A mount for holding a crystal to be examined using X-ray crystallography, said mount comprising:
   a film having a tip end for reception of a crystal; and
   means for imparting curvature to said film to increase the structural rigidity of said film.

2. The mount of claim 1, wherein said film is formed of polyimide and has a thickness of 50 microns or less.

3. The mount of claim 1, wherein said means for imparting curvature to said film comprises a rod having a curved outer surface to which said film is attached.

4. The mount of claim 3, wherein said rod has a beveled or conical top end to increase a viewing angle for a sample crystal.

5. The mount of claim 1, wherein said means for imparting curvature to said film comprises a first rod having a curved outer surface and a second, hollow rod into which said first rod is inserted, said second, hollow rod having a curved inner surface, wherein said film is inserted between said curved outside surface of said first rod and said curved inner surface of said second, hollow rod.

6. The mount of claim 5, wherein said first and second rods each has a beveled or conical top end to increase a viewing angle for a sample crystal.

7. The mount of claim 1, further including:
   a base to which said film is attached; and
   a plastic, semi-rigid, X-ray transparent tube that is pulled over said film and includes a first end affixed to said base in an air tight sealed manner; and, a second sealed end to facilitate controlling the environment to which a sample crystal is exposed.

8. The mount of claim 1, wherein a first, sample aperture is disposed at said tip end of said film.

9. The mount of claim 8, wherein said film further includes a second aperture spaced from said first, sample aperture and connected to said first aperture by a channel for wicking excess liquid from said first, sample aperture.

10. The mount of claim 8, wherein said first, sample aperture is surrounded by a rim at said tip end of said film, said rim having a width of 100 microns or less.

11. The mount of claim 1, wherein said film includes a second, tail end opposite to said tip end, said tail end being tapered to facilitate insertion of said film into a hollow mounting rod.

12. The mount of claim 1, wherein said film further includes means for facilitating automated alignment of a sample crystal in an X-ray beam.

13. The mount of claim 1, wherein said film is comprised of a plurality of polymer layers.

14. The mount of claim 1, wherein said film is treated to produce a hydrophobic or hydrophilic surface.

15. A mount for holding a crystal to be examined using X-ray crystallography, said mount comprising:
   a base having a cylindrical portion extending upwardly from said base;
   a sample crystal holder attached to said cylindrical portion; and
   a plastic, semi-rigid, X-ray transparent tube having: a first end pulled over said crystal holder and said cylindrical portion of said base, thereby making an air tight seal with said base; and, a second sealed end to facilitate controlling the environment to which a sample crystal is exposed.

16. The mount of claim 15, wherein said crystal holder includes a film having a tip end for reception of a sample crystal and means for imparting curvature to said film to increase the structural rigidity of said film.

17. The mount of claim 16, wherein said means for imparting curvature to said film comprises a hollow rod into which said film is inserted, said hollow rod being affixed to said cylindrical portion of said base.

18. The mount of claim 16, wherein said film and said hollow rod are sized such that said hollow rod imparts curvature to said film when said film is positioned therein.

19. The mount of claim 16, wherein said hollow rod includes an inner curved surface and means are provided for holding said film engagement with said inner curved surface.

20. The mount of claim 16, wherein said hollow rod has a beveled top end to increase a viewing angle for said crystal.

* * * * *